US012622682B2

(12) United States Patent
Yang

(10) Patent No.: US 12,622,682 B2
(45) Date of Patent: May 12, 2026

(54) TISSUE CASSETTE READER

(71) Applicant: SAKURA FINETEK U.S.A., INC.,
Torrance, CA (US)

(72) Inventor: Hwai-Jyh Michael Yang, Cerritos, CA
(US)

(73) Assignee: SAKURA FINETEK U.S.A., INC.,
Torrance, CA (US)

( * ) Notice: Subject to any disclaimer, the term of this
patent is extended or adjusted under 35
U.S.C. 154(b) by 554 days.

(21) Appl. No.: 17/988,685

(22) Filed: Nov. 16, 2022

(65) Prior Publication Data

US 2024/0156443 A1     May 16, 2024

(51) Int. Cl.
*A61B 10/00* (2006.01)
*H04M 1/02* (2006.01)

(52) U.S. Cl.
CPC ....... *A61B 10/0096* (2013.01); *H04M 1/0264*
(2013.01)

(58) Field of Classification Search
CPC ............. A61B 10/0096; H04M 1/0264; G06K
7/10722
See application file for complete search history.

(56) References Cited

U.S. PATENT DOCUMENTS

| | | | |
|---|---|---|---|
| 7,133,543 | B2 | 11/2006 | Verwoerd et al. |
| 7,457,481 | B2 | 11/2008 | de la Torre-Bueno et al. |
| 7,793,842 | B2 | 9/2010 | Neeper et al. |
| 7,876,442 | B2 | 1/2011 | Graupner et al. |
| 8,283,176 | B2 | 10/2012 | Bland et al. |

| | | | |
|---|---|---|---|
| 8,315,445 | B2 | 11/2012 | Sorenson et al. |
| 8,341,528 | B2 | 12/2012 | Chaudhary et al. |
| 8,469,275 | B2 | 6/2013 | Dahari |
| | | (Continued) | |

FOREIGN PATENT DOCUMENTS

| | | |
|---|---|---|
| AU | 2018348080 B2 | 11/2020 |
| EP | 3200118 A1 | 2/2017 |
| | (Continued) | |

OTHER PUBLICATIONS

Related Application, Australian patent appl. no. 2023200955, Examination Report No. 2, Dated Jun. 13, 2024.

(Continued)

*Primary Examiner* — Robert J Michaud
(74) *Attorney, Agent, or Firm* — William Thomas Babbitt,
Esq.

(57) ABSTRACT

An apparatus including: a base; a carriage coupled to the
base and projecting a distance above the base, the carriage
operable to contain a mobile phone comprising a camera
array in a position such that the camera array faces in a
direction of the base; and a controller including machine-
readable instructions operable to direct a movement of one
of the carriage and the base in a direction with respect to the
other along an axis. A method including: placing a mobile
phone in a carriage; placing a container below the carriage,
the container comprising a plurality of tissue cassettes; and
capturing by the mobile phone of an image of the identifier
on each of the plurality of tissue cassettes while the plurality
of tissue cassettes remain in the container. Also, a machine-
readable medium including instructions to cause a mobile to
stitch successive captured images of identifiers into an
overall image.

23 Claims, 6 Drawing Sheets

(56) References Cited

U.S. PATENT DOCUMENTS

| | | | |
|---|---|---|---|
| 8,676,509 | B2 | 3/2014 | De La Torre-Bueno |
| 8,722,412 | B2 | 5/2014 | Egle et al. |
| 8,797,396 | B2 | 8/2014 | Dietz et al. |
| 8,969,087 | B2 | 3/2015 | Bland et al. |
| 8,973,293 | B2 | 3/2015 | Palmer et al. |
| 9,117,024 | B2 | 8/2015 | De La Torre-Bueno |
| 9,122,905 | B2 | 9/2015 | Soenksen et al. |
| 9,285,380 | B2 | 3/2016 | Kasai et al. |
| 9,322,767 | B2 | 4/2016 | Ehrenkranz |
| 9,384,192 | B2 | 7/2016 | Von Bueren et al. |
| 9,519,847 | B2 | 12/2016 | Pedrazzini |
| 9,659,153 | B2 | 5/2017 | De La Torre-Bueno |
| 9,747,326 | B2 | 8/2017 | Tanba et al. |
| 9,787,815 | B2 | 10/2017 | Erickson et al. |
| 9,864,888 | B2 | 1/2018 | Hughes |
| 10,088,655 | B2 | 10/2018 | Virk et al. |
| 10,498,936 | B2 | 12/2019 | Ehrenkranz |
| 10,706,247 | B1 * | 7/2020 | Miller .................. G06K 7/1413 |
| 10,734,099 | B2 | 8/2020 | Evans et al. |
| 11,054,431 | B2 | 7/2021 | Merlo et al. |
| 11,071,978 | B2 | 7/2021 | Crum et al. |
| 11,231,348 | B2 | 1/2022 | Visinoni et al. |
| 11,275,914 | B2 | 3/2022 | Hagen et al. |
| 2003/0141443 | A1 | 7/2003 | Spears et al. |
| 2006/0159325 | A1 | 7/2006 | Zeineh et al. |
| 2008/0113440 | A1 | 5/2008 | Gurney et al. |
| 2010/0086964 | A1 | 4/2010 | Walter et al. |
| 2010/0167334 | A1 | 7/2010 | Williamson, IV |
| 2013/0065797 | A1 | 3/2013 | Silbert et al. |
| 2014/0068442 | A1 | 3/2014 | Eichhorn et al. |
| 2014/0098252 | A1 | 4/2014 | Chang et al. |
| 2014/0188545 | A1 | 7/2014 | Chirica et al. |
| 2014/0273085 | A1 | 9/2014 | Eckert et al. |
| 2014/0291400 | A1 | 10/2014 | Olmstead et al. |
| 2015/0099306 | A1 | 4/2015 | Ku |
| 2016/0085913 | A1 | 3/2016 | Evans et al. |
| 2016/0187236 | A1 | 6/2016 | Berberich et al. |
| 2016/0188937 | A1 | 6/2016 | Tyrrell et al. |
| 2016/0210486 | A1 | 7/2016 | Porreca et al. |
| 2016/0232391 | A1 * | 8/2016 | Wilhelm ............ A61B 10/0096 |
| 2017/0177913 | A1 | 6/2017 | Benedetti et al. |
| 2017/0293719 | A1 | 10/2017 | Roig Munill et al. |
| 2018/0226138 | A1 | 8/2018 | Leavitt et al. |
| 2019/0105021 | A1 | 4/2019 | Von Bueren et al. |
| 2020/0287416 | A1 * | 9/2020 | Sauterel .............. G06F 3/03543 |
| 2020/0341019 | A1 | 10/2020 | Cinti |
| 2020/0365241 | A1 | 11/2020 | Evans et al. |
| 2021/0136722 | A1 | 5/2021 | Scialo et al. |
| 2021/0140857 | A1 | 5/2021 | Tarbet et al. |
| 2021/0192265 | A1 * | 6/2021 | Fleischmann .... G01N 35/00732 |
| 2021/0390275 | A1 | 12/2021 | Xie et al. |
| 2022/0001605 | A1 | 1/2022 | Okamoto et al. |
| 2022/0160581 | A1 | 5/2022 | Rigby |

FOREIGN PATENT DOCUMENTS

| | | |
|---|---|---|
| ES | 2529514 B1 | 2/2015 |
| IN | 2014/130592 A1 | 8/2014 |
| JP | H10227797 A | 8/1998 |
| JP | 2013088116 A | 5/2013 |
| JP | 2020-537127 A | 12/2020 |
| JP | 2022-508799 A | 1/2022 |
| WO | 2014/130592 A1 | 8/2014 |
| WO | 201974941 A1 | 4/2019 |
| WO | 2022117094 A1 | 6/2022 |

OTHER PUBLICATIONS

Related Japanese patent application No. 2023-021343, Notice of reasons for refusal, Dated: Apr. 22, 2024.

Related Application, Australian patent appl. no. 2023200955, Examination Report No. 1, Dated Nov. 30, 2023.

Sakura Finetek U.S.A., Inc., Related Application, Canadian Patent Application No. 3077707, Notice of Allowance, Dated Dec. 23, 2021.

Sakura Finetek U.S.A., Inc., Related Application, European Patent Application No. 18793345.2, Communication pursuant to Article 94(3) EPC, Dated Apr. 19, 2022.

Dmag Romania: "Scandit Barcode Scanner SDK 5 2 Includes MatrixScan Premium", YouTube, Jul. 6, 2017 2017-07-06), XP055544932.

Sakura Finetek U.S.A., Inc., Related Application, Chinese Patent Application No. 2018800656587, Notice of Allowance, Dated Apr. 24, 2022.

Related Application, European patent appl. No. 23175891.3, Communication pursuant to article 94(3) EPC, Dated Mar. 13, 2025.

Related Application, Japanese patent application No. 2023-021343, Notice of reasons for refusal, Dated: Oct. 29, 2024.

Related application, U.S. Appl. No. 16/154,634, Office Action, Dated Mar. 27, 2025.

Related application, U.S. Appl. No. 16/154,634, Office Action, Dated Sep. 05, 2024.

Related application, U.S. Appl. No. 16/154,634, Office Action, Dated Mar. 15, 2024.

Related application, U.S. Appl. No. 16/154,634, Office Action, Dated Oct. 26, 2023.

Related application, U.S. Appl. No. 16/154,634, Office Action, Dated Jun. 29, 2023.

Related application, U.S. Appl. No. 16/154,634, Office Action, Dated Apr. 28, 23.

Related application, U.S. Appl. No. 16/154,634, Office Action, Dated Jan. 27, 2023.

Related application, U.S. Appl. No. 16/154,634, Office Action, Dated Oct. 11, 2022.

Paul Williams, Leica Biosystems CEREBRO automated sample tracking, 2015, The Pathologist (Year: 2015).

Related application, U.S. Appl. No. 16/154,634, Office Action, Dated Jun. 17, 2022.

Related Application, European Patent Office Application No. 18 793 345.2-1001, Communication pursuant to Article 94(3) EPC, Mailed On Oct. 1, 2025.

Related Application, Chinese Patent Application No. 2018800656587, Sakura Finetek U.S.A., Inc., First Office Action, Dated Apr. 24, 2022.

Related Application, Brazil Patent Application No. BR112020006429-7, Sakura Finetek U.S.A., Inc., Preliminary Office Action, Dated Oct. 31, 2023.

Related Application, European Patent Application No. 18793345.2-1001, Sakura Finetek U.S.A., Inc., Communication Pursuant To Article 94(3) EPC, Dated Sep. 26, 2023.

Related Application, Chinese Patent Application No. 2018800656587, Sakura Finetek U.S.A., Inc., Decision of Rejection, Dated Feb. 11, 2023.

Related Application, Chinese Patent Application No. 201880065658.7, Sakura Finetek U.S.A., Inc., Second Office Action, Dated Nov. 16, 2022.

Related Application, Sakura Finetek U.S.A., Inc.; European Patent Application No. 18793345.2, Communication pursuant to Article 94(3) EPC, Dated: Feb. 15, 2023.

Idmag Romania: "Scandit Barcode Scanner SDK 5 2 Includes MarixScan Premium", YouTube, Jul. 6, 2017, XP055544932.

Related Application, Sakura Finetek U.S.A., Inc.; Chinese Patent Application No. 201880065658.7, Decision of Rejection, Dated Feb. 11, 2023.

Related Application, European Patent Application No. 18793345.2-1001, Sakura Finetek U.S.A., Inc., Communication Pursuant To Article 94(3) EPC , Dated Oct. 23, 2024.

Irelated Application, Brazil Patent Application No. BR112020006429-7, Examination Report, Dated Feb. 21, 2024.

Int'l Search report, Patent Cooperation Treaty, PCT/US2018/055037, Jan. 25, 2019.

Idmag Romania: "Scandit Barcode Scanner SDK 5 2 Includes MatrixScan Premium", YouTube, Jul. 6, 2017, XP055544932 Retrieved from the Internet: URL:https://www.youtube.com/watch?v=xe0NuLFC9_o.

(56)     References Cited

OTHER PUBLICATIONS

Written Opinion of the Int'l Searching Authority, PCT/US2018/
055037.

* cited by examiner

AUTOMATICALLY IMAGE/SENSE IDENTIFIER ON EACH CASSETTE

TISSUE CASSETTE READER

TECHNICAL FIELD

Tissue processing and carrier identification.

BACKGROUND

Tissues from the body taken for diagnosis of disease processes are often processed in the histology laboratory to produce paraffin blocks embedding them to then cut thin tissue sections which can be mounted on slides, stained and viewed under a microscope by a pathologist for analysis. These pre-analytical processes generally include, in order, gross examination, fixation, dehydration, clearing, paraffin infiltration and embedding. The procedure is used for processing tissues including biopsies, larger specimens removed at surgery, or tissues from autopsy.

Gross examination generally consists of describing the macroscopic specimen and placing all or selected parts of it into a sample carrier such as a small plastic cassette which holds the tissue while it is being processed to a paraffin block. Initially, the cassettes are placed into a fixative.

Following gross examination, the fixation of the tissue continues. A purpose of fixation is to preserve tissues permanently in as life-like a state as possible by altering structures of proteins such that degradation by autolysis does not occur. Once the tissue has been fixed or fixated, the tissue needs to be processed into a form in which it can be made into thin sections for microscopic examination. The usual way this is done is with paraffin. Embedding tissue in paraffin provides a solid support matrix for the tissue allowing it be sectioned at a thickness on the order of 1 to 20 microns. Getting fixed tissue into paraffin for sectioning is called tissue processing with the main steps in this process being dehydration, clearing, infiltration, which then is followed by embedding.

Tissues fixed in aqueous solutions cannot be directly infiltrated with paraffin. First, the water from the tissues must be removed by dehydration. This may be done with a series of alcohols at different concentrations (e.g., 70 percent to 95 percent to 100 percent). Alternatively, the dehydration may be done with a mixture of formalin and alcohol. Other dehydrants can also be used such as acetone or mixtures of different solvents.

Following dehydration, the tissue is cleared. "Clearing" consists of removal of the dehydrant and some of the lipids with a substance that will be miscible with the embedding medium (e.g., paraffin). The most common clearing agent is xylene.

Once cleared, the tissue is infiltrated with an embedding agent such as paraffin. Finally, the tissue in a cassette or removed from its cassette is placed into molten paraffin and then the paraffin is cooled to form a solidified block embedding or encapsulating the tissue so that it can be sectioned. Alternatively, the tissue can be processed in a sectionable cassette, embedded in paraffin along with the cassette and sectioned. Once the tissue has been embedded in a solid paraffin block, the tissue can be cut into sections that can be placed on one or multiple slides. This is done with a microtome. Once sections are cut, they are floated on a warm water bath that helps remove any wrinkles. The tissue sections in paraffin are then picked up from the water bath and placed on a glass microscope slide.

A sample carrier such as a cassette may be marked with identification and/or process information. The introduction of barcodes has made it possible to machine read barcodes printed on a sample carrier and to track the sample carrier during histological sample processing, embedding, sectioning and any verifications steps from creation to archiving.

BRIEF DESCRIPTION OF THE DRAWINGS

Embodiments are illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

DETAILED DESCRIPTION

An automated device or apparatus operable to obtain information from a sample carrier such as an identifier on a sample carrier such as a tissue cassette is disclosed. In one embodiment, the device is operable to sense identification information (an identifier) such as a barcode on a display area of a single cassette while the cassette is present with other cassettes in an assembly such as a magazine or basket or container. In another embodiment, the device or apparatus is operable to capture an image (e.g., a two-dimensional image of identifiers on multiple cassettes in an assembly. Each identifier whether sensed individually or captured in an image of identifiers of multiple cassettes is then read, correlated to the relative locations of cassettes inside the magazines or basket or container, and optionally stored. The read, correlated and optionally stored information regarding an identifier may be used for quality control, routing and tracking of cassettes in a laboratory (e.g., a histopathology laboratory).

Figure 1:
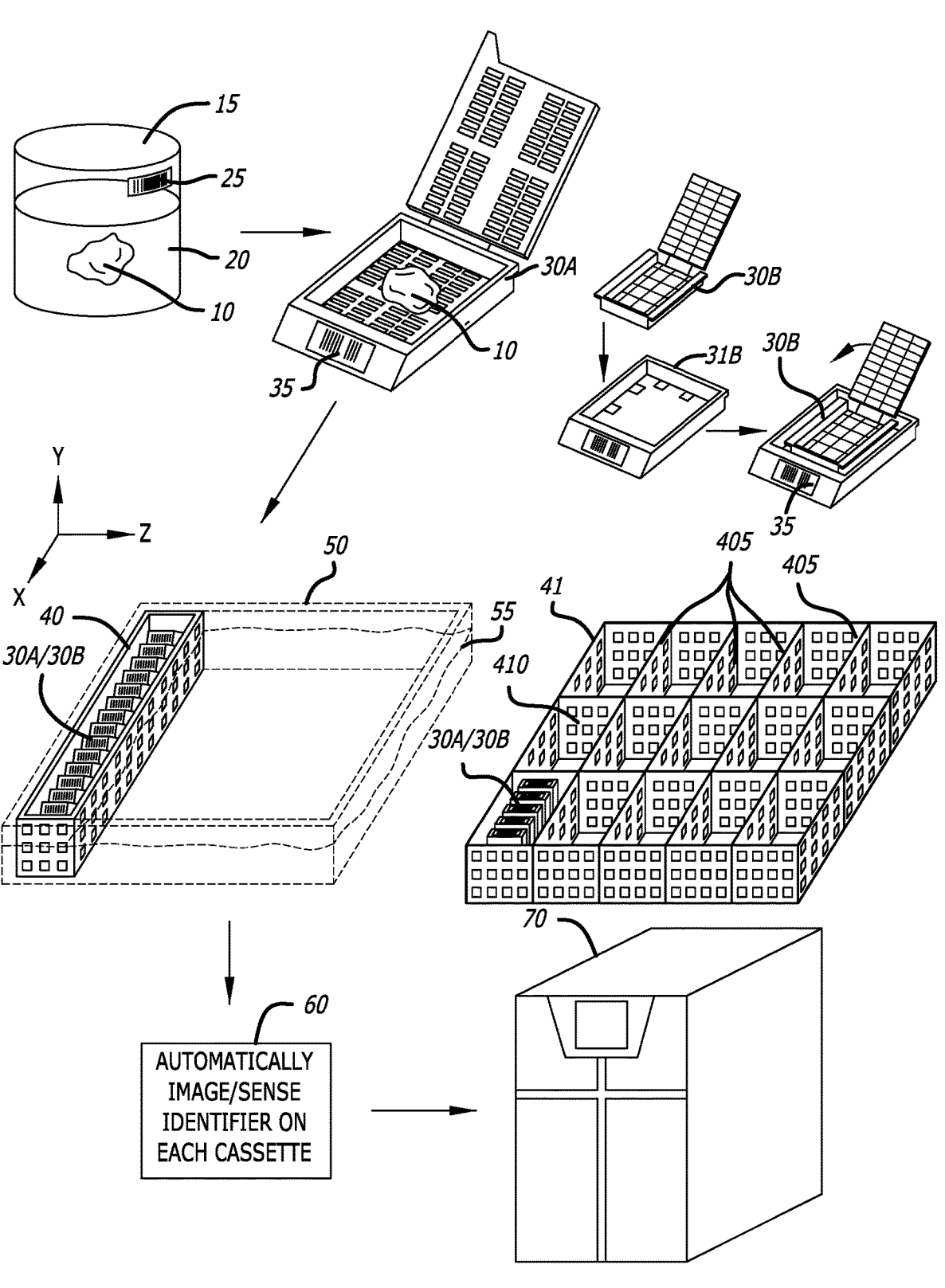
FIG. 1 shows an illustrative process flow of preparing a tissue taken from a subject for tissue processing.

FIG. 1 illustratively shows a representative initial process flow of a tissue sample processing described above (e.g., prior to dehydration, clearing, paraffin infiltration and embedding). FIG. 1 shows tissue sample 10 that has been, for example, taken from a body (e.g., a human body) and placed in container 15 and immersed in fixative 20 such as formalin. In one example, tissue sample 10 may be obtained in a medical procedure by a physician that desires the tissue sample be evaluated for diagnostic or forensic purposes (e.g., evaluated for the presence of a disease). Container 15, in this embodiment, includes identifier 25 such as barcode that representatively contains or references information such as a name of the patient from where the tissue was extracted, physician identification information and optionally the desired processing protocol.

Prior to evaluation for diagnostic or forensic purposes, tissue sample 10 is subjected to tissue processing. To prepare for tissue processing, tissue sample 10 may be transferred, in whole or in part, from container 15 into a cassette. FIG. 1 shows two examples of cassettes. Cassette 30A is generally a rectangular box of a rigid polymer material having an interior volume defined by sidewalls and a base and having a retractable, hinged lid. A front sidewall or face of cassette 30 may be disposed at, for example, a 30-50 degree angle, such as a 45 degree angle, relative to the base with the other sidewalls at approximately a 90 degree angle relative to the base. One example of cassette 30A is a Tissue-Tek® Uni-Cassette® commercially available from Sakura Finetek USA, Inc. of Torrance, California. A Tissue-Tek® Uni-Cassette® has an exterior width dimension of 28 millimeters (mm), an exterior length of 41 mm and an exterior height of 6 mm. Cassette 30B is a two-part cassette system or assembly including rectangular frame 31B and a cassette of a material that has sectioning characteristics similar to paraffin. Frame 31B includes sidewalls of a rigid polymer material and no lid or base. A front sidewall or face of frame 31B may be disposed at, for example, a 30-50 degree angle, such as a 45 degree angle, relative to the base with the other sidewalls at approximately a 90 degree angle relative to the base. The cassette includes a rectangularly-shaped body including an interior volume defined by sidewalls and a base and a retractable, hinged lid. The cassette sidewalls include an upper outwardly projecting flange that, when the cassette is inserted into the frame to form the assembly, the flange catches on inward projections on the frame to retain the cassette in the frame. One example of cassette 30B is a Tissue-Tek® Paraform® sectionable cassette that fits into a Tissue-Tek® Paraform® frame, both the cassette and frame commercially available from Sakura Finetek USA, Inc. A Tissue-Tek® Paraform® sectionable cassette and frame assembly has exterior width and length dimensions similar to a Tissue-Tek® Uni-Cassette® cassette but may have an exterior height dimension slightly less as there is no rigid polymer lid. For the discussion herein, unless otherwise noted, a "cassette" such as cassette 30A or cassette 30B includes a unitary cassette as in the Tissue-Tek® Uni-Cassette® or a cassette assembly as in the Tissue-Tek® Paraform® sectionable cassette that fits into a Tissue-Tek® Paraform® frame.

As shown in FIG. 1, each of cassette 30A and cassette 30B includes identifier 35 such as a barcode that contains or references information such as patient information, physician information and optionally processing protocol for the tissue sample is affixed by a technician to the front sidewall or face of cassette 30. A representative barcode may be a one-dimensional (1D) barcode or a two-dimensional (2D) barcode. Identifier 35 is illustrated as a 1D barcode. Identifier 35 may be printed directly on the front sidewall or face of the cassette or frame in the case of a cassette assembly (e.g., frame 31B), may be printed on a label that is affixed to the front sidewall or face of the cassette or frame with an adhesive or may be etched into the material of the front sidewall or face of the cassette or frame.

Once tissue sample 10 or a portion thereof is contained in cassette 30A or cassette 30B/frame 31B with the corresponding lid closed, the cassette may be placed in an array with other cassettes that, for example, maybe subjected to a similar tissue processing protocol. One type of an array is magazine 40. Magazine 40 is a rectangular container of a metal or polymer material including a volume defined by opposing sidewalls and a base. Magazine 40 has a lateral or width dimension (z-dimension) therein to accommodate no more than a single cassette positioned laterally and a longitudinal or length dimension (x-dimension) to accommodate several cassettes (e.g., 16 cassettes, 20 cassettes) each aligned or stacked base to top/lid. Representative magazines include Tissue-Tek AutoTEC® magazines and Tissue-Tek Xpress® magazines of Sakura Finetek USA, Inc. A Tissue-Tek Xpress® magazine has a length (z) dimension of 6⅛ inches (156 millimeters (mm)), a width (x) dimension of 1⅜ inches (35 mm) and a height (y) dimension of 1⅞ inches (48 mm).

In another example, cassette 30A or cassette 30B/frame 31B (with the respective lid closed) may be placed in an array that is tissue cassette basket 41 such as a cassette basket used in a Tissue-Tek VIP® tissue processor, commercially available from Sakura Finetek USA, Inc. Basket 41 may be a metal or plastic rectangular container including pairs of opposing sidewalls and a base that define a volume. Basket 41 does not have a lid. Ones of the opposing sidewalls and base may be perforated preventing the sidewalls and base of basket 41 from retaining a volume of a liquid therein. Basket 41 also includes partitions of a similar material (and possibly perforated) in the volume. FIG. 1 shows basket 41 representatively including four longitudinal partitions 405 creating five longitudinal columns and two lateral partitions 410 creating three lateral rows. Partitions 405 and partitions 410 together with the sidewalls of basket 41 define segments, with each segment including a lateral or width dimension (z-dimension) therein to accommodate no more than a single cassette positioned laterally and a longitudinal or length dimension (x-dimension) to accommodate several cassettes (e.g., 10 Tissue-Tek® Uni-Cassette® or 12 Tissue-Tek® Paraform® cassettes in each segment). A Tissue-Tek VIP® tissue processor basket has a length (x) dimension of 8.7 inches (222 mm), a width (z) dimension of 5.9 inches (151 mm) and a height (y) dimension of 1.8 inches (46 mm).

As illustrated in FIG. 1, each cassette is placed in magazine 40 or basket 41 in an upright or longitudinal position so that the front sidewall or face of each cassette faces out the top of magazine 40 or basket 41 as viewed. The cassettes are preferably placed so that the angled front sidewall or face of each cassette is oriented similarly (e.g., a base of a cassette is oriented next to or contacts a top/lid of an adjacent cassette).

Referring to FIG. 1, magazine 40 or basket 41 may be placed into container 50 that includes a volume of fixative (fixative 55) in a volume therein to inhibit tissue samples in individual cassettes from drying out and/or allow the tissue samples to continue to be fixed or fixated. Magazine 40 or basket 41 may be placed into container 50 prior to loading cassettes into the magazine or the basket as the case may be. Magazine 40 can reside in container 50 either alone or with other magazines. Basket 41 such as a Tissue-Tek VIP® tissue processor basket may have dimensions that occupy substantially all of the area of container 50 so may reside in container 50 solely. A basket smaller than a Tissue-Tek VIP® tissue processor basket may possibly reside in container 50 with another basket if the dimensions allow. Container 50 may include features such as tabs that direct an alignment of a magazine in the container. In one embodiment, container 50 includes sidewalls and a base that define a volume. A top surface of container 50 may be exposed (no lid). Container 50 may further include features to identify what type of cassette container is to be placed inside, either magazines 40 or basket 41.

According to one example, once the cassettes each containing a tissue sample are contained in a magazine or basket and optionally in container 50, the identifier associated with each cassette (on a front sidewall or face) may be automatically sensed by a device or apparatus that is operable to identify an identifier on an individual cassette (block 60, FIG. 1). The identifier on each cassette may be sensed while the cassette remains in a magazine or basket in container 50. A level of a fluid in container 50 may be reduced prior to sensing of identifiers if desired. The sensing of identifiers on cassettes may be done individually by, for example, automatically positioning a camera over each cassette in a magazine or basket in container 50 or sensed collectively by, for example, sensing (e.g., photographing) an image of multiple cassettes in a magazine or individual or multiple cassettes in multiple magazines or multiple cassettes in a basket (e.g., cassettes in z-direction rows distinguished by individual magazines or distinguished by longitudinal partitions 405 of basket 41). Sensing identifiers associated with cassettes at this time identifies each tissue sample prior to tissue processing. Such feature offers a quality control function by providing a check that a cassette or cassettes in a magazine or basket destined for a particular tissue processing protocol are intended for that protocol. For example, a reference cassette may be placed in a magazine or basket. A reference cassette may include an identifier that associates the magazine or basket with a particular tissue processing protocol (e.g., cassette 30E, FIG. 1). The identifier information read from the reference cassette may be compared with identifier information of each of the other tissue cassettes in the particular magazine or basket. If after the comparison, the identifiers on all the cassettes in the magazine or basket share the same tissue processing protocol as the reference cassette, the tissue processing protocol is initiated on all the cassettes. If the identifier on one or more cassettes in the magazine does not share the same tissue processing protocol as the reference cassette, such one or more cassettes can be removed from the magazine or basket before tissue processing. Sensing identifiers prior to tissue processing also offers a tracking function in the sense that a location of a tissue sample is known. Sensing identifiers prior to tissue processing also offers a routing function where the cassettes have been identified for a particular tissue processing protocol which may serve to alert a technician as to the protocol to perform on the cassettes. Sensing identifiers prior to tissue processing also minimizes a risk that the same identifier could be present on two cassettes (printing duplicate identifiers). It is desired that each cassette contain a unique identifier. If two cassettes mistakenly contain the same identifier (e.g., the same barcode), the mistake may be identified and corrected before processing by sensing identifiers.

Following the sensing of an identifier for each cassette in magazine 40 or basket 41, the magazine or basket may be placed in a tissue processor 70 such as Tissue-Tek VIP® tissue processor or Xpress®. A tissue processor such as tissue processor 70 may proceed with one more or more steps of fixing a tissue sample (e.g., dehydration, clearing, infiltrating).

Figures 2, 3:
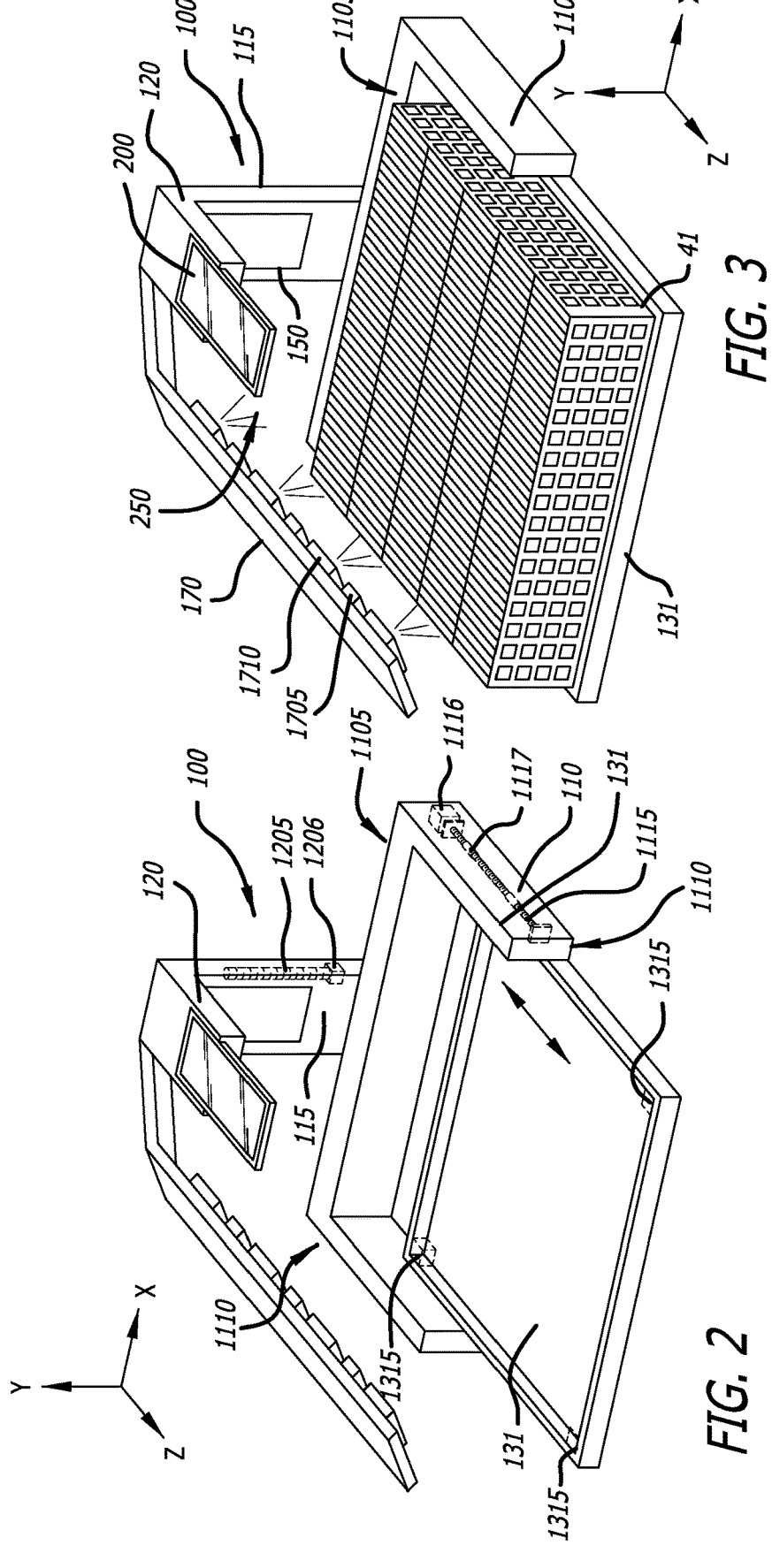
FIG. 2 shows a top, side perspective view of a device that may be used to capture, store and output identification information such as a barcode on a sample carrier (e.g., a cassette or cassette/frame assembly) in an array such as in a basket, a magazine or other container without removing the sample carrier from the array (e.g., magazine, basket or other container).
FIG. 3 shows the device of FIG. 2 a mobile phone is placed in a carriage of the device and a basket containing tissue cassettes is contained in a base of the device.

FIG. 2 shows a top side perspective view of an electronic device or apparatus that can sense, read, store and output information such as a barcode on a sample carrier (e.g., tissue cassette) or information contained in a barcode on a sample carrier. Device 100 is operable to be mounted on a table or other surface and have sample carriers such as cassettes be brought to the device. Device 100 includes base 110 and carriage 120 connected to base 110 through support or pedestal 115. Carriage 120 may be operable to contain a mobile phone, such as mobile phone 200. A mobile phone or smartphone is a wireless handheld device that can run software programs or applications. A mobile phone or smartphone has an operating system such as iOS (Apple), Android (Google) or Windows Phone (Microsoft), a memory (e.g., flash memory) capable of storing programs or applications and data, and a camera (including but not limited to one or more lenses, an automatic focus, a flash, and a sensor to convert focused photons of light into an electrical signal). Examples of a mobile phone include but are not limited to Apple iPhone (e.g., iPhone 12, iPhone 13, iPhone 13 Mini, iPhone 14), Google Pixel 7, Samsung Galaxy S22 and ASUS ZenFone 9. A mobile phone or smartphone as used herein includes a tablet, such as, but not limited to, an Apple iPad or iPad Pro, a Samsung Galaxy S8, and a Microsoft® Surface Pro 8 that may or may not have basic telephony.

Carriage 120 of device 100 includes for example, a cradle that may representatively have a width dimension (x-dimension) of 6 centimeter (cm) to 25 cm and a length dimension (z-dimension) of 15 cm to 31 cm. The cradle defines a frame upon which a mobile phone may be placed and supported horizontally (an xz plane). Within the frame is an opening through which a camera lens or lenses of the mobile phone may be unobstructed to view/sense/image an area below the cradle when the mobile phone is placed in the cradle. Alternatively, as shown in FIG. 2, a z-dimension of the cradle of carriage 120 may be configured so that when mobile phone 200 is seated in the cradle, a portion of a length of the mobile phone including a lens or lenses extends in a z-direction beyond the carriage 120 and is supported by carriage 120 in a cantilever fashion. As illustrated in FIG. 2, carriage 120 projects a vertical or y-dimension distance from base 110 defined by a length of support or pedestal 115. A distance may be determined by a distance for a camera of a mobile phone to capture an image of an identifier on a cassette when the cassette is in a magazine or basket or other container below the cradle. In one example, a distance may be determined by the lens or lenses on the mobile phone to allow one screen image to encompass an entire width of a basket 41 or container 50 (a z-dimension) plus some margin. Representatively for 1× lens of a mobile phone, a representative distance is, for example, 10 cm to 18 cm, such as 12 cm to 16 cm, such as 14 cm for an iPhone 12.

It is appreciated that there are different manufacturers of mobile phones currently commercially available. Such phones may have a camera feature including lenses that may vary a distance a particular phone needs to be from basket 41 or container 50 placed in device 100 to, for example, allow one screen image to encompass an entire width of a basket 41 or container 50 plus some margin. Pedestal 115 may include a feature allowing its y-direction length to be changed depending on the phone model that will be placed in carriage 120. Such feature may include ball screw 1205 extending in a y-direction within a body of pedestal 115. Ball screw 1205 may be connected to a body of pedestal 115 and to motor 1206. Rotation of ball screw 1205 by motor 1206 may cause pedestal 115 (and carriage 120) to move up or down. Alternatively, carriage 120 may be configured for a particular mobile phone. A distance a lens or lenses of the mobile phone are from basket 41 or container 50 placed in device 100 may be determined by carriage 120. For example, one carriage might attach to pedestal 115 so that phone (e.g., phone 200) is a greater distance from basket 41 or container 50 in device 100 than another carriage.

Base 110 of device 100 includes an orientation designation for a container, such as basket 41 or container 50 operable to contain one or more magazines 40 and/or operable to contain basket 41. Base 110 of device 100 may be in the form of spine 1105 projecting in an x-direction from a length that is slightly greater than a length of a container (e.g., 0.2 inches greater, 0.5 inches greater or larger, to accommodate a width of a basket 41 or container 50. At each end of spine 1105 are legs 1110 projecting from spine 1105 in a perpendicular direction (z-direction). Each leg 1110 may project a z-direction distance less than, equivalent to or greater than a z-direction width of a container or basket operable to be oriented between the legs. A x-direction distance between legs 1110 might be greater than an x-direction width of a container or basket, for example, to accommodate a desired x-direction travel of pedestal 115 and phone 200 to position a lens or lenses over a cassette identifier that might be in the container or basket and perhaps cannot be read without the lens or lenses being directly over the cassette. Spine 1105 and legs 1110 define two adjacent rectangular corners into which a container (e.g., container 50) or basket (e.g., basket 41) may be bounded on three sides. FIG. 3 shows device or apparatus 100 of FIG. 2 including basket 41 therein contained within device 100 by spine 1105 and legs 1110. Basket 41 may include a portion, including an entire portion of the contents of the basket filled with cassettes (e.g., cassette 30A and/or cassette 30B/frame 31B).

Device 100 may also include drip tray 131 having dimensions (xz dimensions) to fit between legs 1110. Drip tray 131 may include pairs of opposing sidewalls and a base that collectively define a volume therein. A length dimension (x-dimension) and width dimension (z-dimension) of drip tray 131 may be selected so that a container (e.g., container 50) or basket (e.g., basket 41 (also a container)) fits within the volume of the drip tray as shown in FIG. 3 (basket 41 in drip tray 131). When positioned between legs 1110 of base 110, drip tray 131 may be connected to one or both legs 1110 and/or spine 1105. For example, one or more sidewalls of drip tray 131 may include a top edge lip or externally projecting protrusion or flange that corresponds to a groove in legs 1110 and/or spine 1105.

Drip tray 131 may include an orientation designation for container 50 and/or basket 41 alone (i.e., a basket not in container 50). An orientation designation may be projections 1315 on the inside sidewalls of drip tray 131. Representatively, drip tray 131 may have opposing sidewalls defining a volume therein. Projections 1315 may be placed at the base of corners of the sidewalls. Projections 1315 may define a xz diameter for basket 41 in drip tray 131 within an area bounded by the projections. Container 50 may have xz dimensions larger than basket 41. Container 50 may be positioned within a volume of drip tray 131 on (above) projections 1315. Container 50 or basket 41 in one example may be placed in drip tray with a single orientation for cassettes. As seen in FIG. 3, such orientation may be that partitions 405 of basket 41 (seated in drip tray 131 in FIG. 3) extend in an x-direction. Where basket 41 or container 50 is a rectangle that is oblong (i.e., equiangular quadrilateral that is not a square), partitions 405 extend the length of the longer sides. Drip tray 131 may dimensions that accommodate basket 41 or container 50 only in a desired single orientation by, for example, having a x-direction length greater than a z-direction length.

In one example, drip tray 131 may be operable to move in a z-direction. An inset of FIG. 2 shows one leg 1110 (a right leg as viewed) having an outer wall removed. Inside leg 1110 is lead screw 1115 that is driven by electrically powered motor 1116. The inset shows drip tray 131 connected to lead screw 1115 by threaded connectors 1117 (e.g., female threaded connectors to match male threads on lead screw 1115). A similar lead screw and threaded connectors may be present in the other leg 1110 (the left leg as viewed). The motorized lead screw system is operable to move drip tray 131 away from or toward spine 1105 (z-direction movement). Although a lead screw system is shown, it is appreciated that other forms of motorized z-direction movement of drip tray 131 may be utilized. Other examples include, but are not limited to, a ball screw system or a belt drive system.

Figure 4:
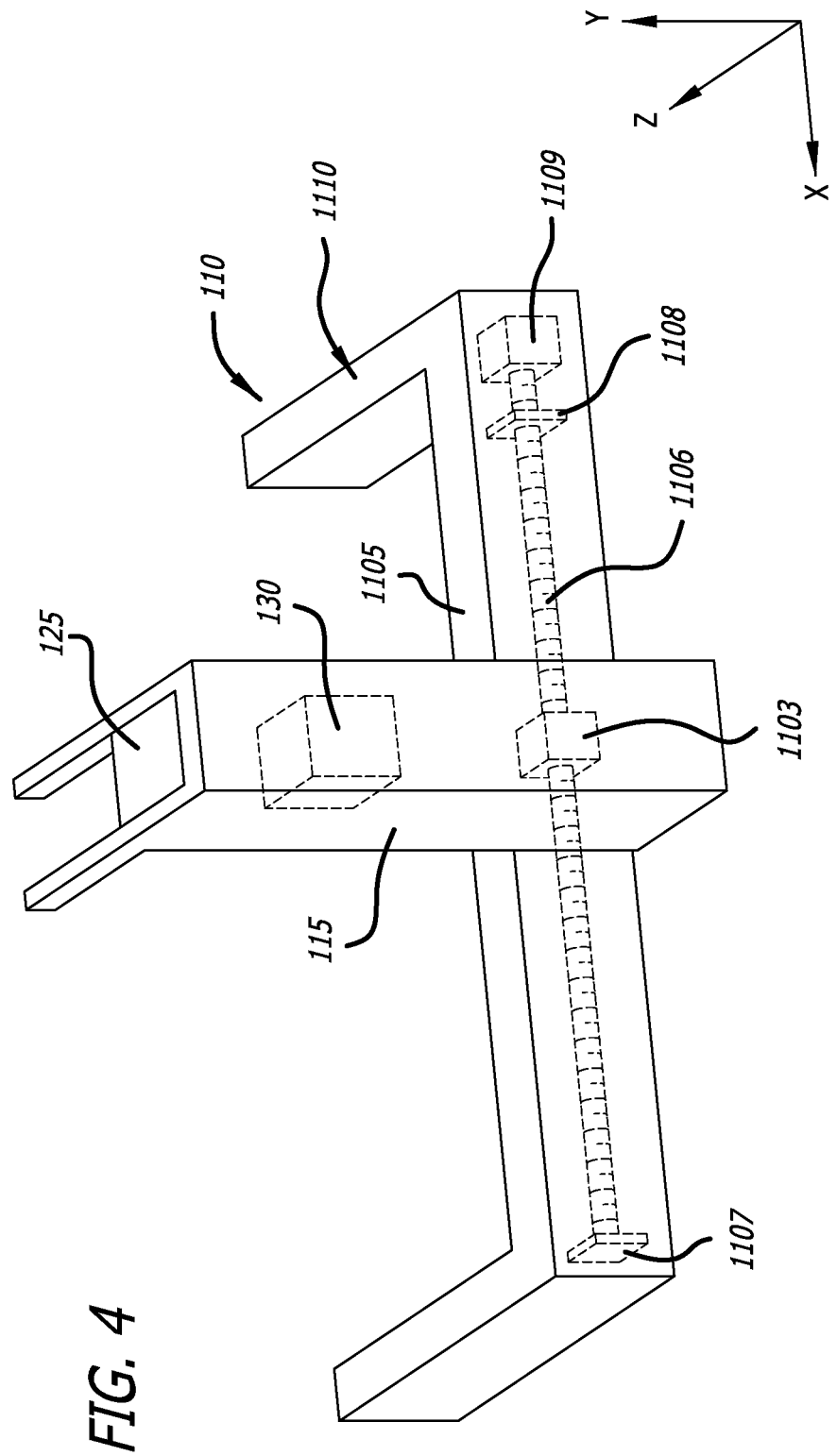
FIG. 4 shows a top, back perspective view of the device of FIG. 2.

One of support or pedestal 115 (and accordingly carousel 120) and base 110 may be operable to move longitudinally (x-direction) with respect to the other. FIG. 4 shows a perspective, back-side view of device 100 with portions of base 110 (portions of spine 1105) and support or pedestal 115 cut away to expose components inside. In this example, support or pedestal 115 moves longitudinally (in an x-direction) with respect to base 110. FIG. 4 shows a cut-away view of a backside of base 110. Inside a body of base 110 extending, for example, a length of spine 1105 is lead screw 1106. Lead screw 1106 extends substantially a length (x-direction) of spine 1105 and is supported at each end by bracket 1107 and bracket 1108, respectively. Lead screw 1106 is connected to motor 1109 and motor 1109 is operable to rotate lead screw 1106. Motor 1109 is electrically connected to controller 130 and a power source (not shown). FIG. 4 also shows bracket 1103 connected to lead screw 1106 and support or pedestal 115. Rotation of lead screw 1106 by motor 1109 (clockwise or counterclockwise) will cause longitudinal (x-direction) movement of support or pedestal 115. It is appreciated that longitudinal movement of support or pedestal 115 with respect to base 110 may be reversed such as by fixing support or pedestal 115 and using a lead screw to move base in a lateral direction. Although a lead screw system is shown, it is appreciated that other forms of motorized z-direction movement of pedestal 115 or base 110 may be utilized. Other examples include, but are not limited to, a ball screw system or a belt drive system.

As noted above, device 100 is operable to support and/or contain a mobile phone in carriage 120. As shown in FIG. 3, mobile phone 200 is positioned in carriage 120 so that it is in an xz plane. FIG. 3 shows mobile phone 200 in carriage 120 in a screen side upward configuration. Mobile phone 200 includes a camera array extending to its backside (not viewed) including a lens or lenses and sensor(s). Mobile phone 200 may also include a flash or light that, when activated, directs a light from a backside of the mobile phone. Device 100 may also include a power source to charge/recharge mobile phone 200. FIG. 2 and FIG. 3 show recharger 150 connected to support or pedestal 115. A base of carriage 120 includes charging pod 125 that is a wireless charger for mobile phone 200. Charging pod 125 is connected, for example, through an electrical wire connection to recharger 150. Charging pod 125 creates a magnetic field that mobile phone 200 absorbs to gain energy when placed on the charging pod. The magnetic field produced by charging pod 125 may also be used to position mobile phone 200 in a desired orientation in carriage 120.

Device 100 including mobile phone 200 is operable to sense, capture and interpret an identifier on a cassette (identifier 35 on cassette 30A or cassette 30B). Device 100 includes controller 130 illustrated in pedestal 115 in FIG. 4. Controller 130 may be connected to an electrical power source. Controller 130 may include machine-readable, non-transitory instructions that when executed allow it to communicate with mobile phone 200 and direct a movement of one of support or pedestal 115 (and thus carriage 120) and base 110 in a longitudinal direction (x-direction, FIG. 3) with respect to the other as well as a z-direction movement of drip tray 131 and possibly a y-direction movement of carriage 120. The motors or moving axes associated with x-, y- and z-direction movement can each have an encoder installed therein (an encoder that generates pulses receivable by controller 130). When, for example, motor 1109 rotates for longitudinal movement (x-direction) of pedestal 115 or base 110, the distance traveled can be known to controller 130 by counting the number of encoder pulses generated. The distance traveled may be used by controller 130 to map the positions of cassettes inside the basket, magazine or containers.

Mobile phone 200 may be placed in carriage 120 and connected to controller 130 (see FIG. 4) either through an electrical cord or through a wireless technology such as the wireless technology standard Bluetooth®, identified by IEEE 802.15.1 or WiFi™ based on IEEE 802.11. Mobile phone 200 may contain non-transitory, machine-readable instructions that, when executed, allow for communication with controller 130 and direct mobile phone 200 contained in the carriage 120 to capture images of identifiers on a plurality of tissue cassettes in a field of view of a camera array of the camera. Such instructions may also include instructions to read the captured images of identifiers, correlate the images to the relative locations of cassettes inside the magazines or basket, generate an overall image from a plurality of sub-images and optionally store the images and identifier information.

Referring to FIG. 2, an assembly including device 100 and basket 41 oriented within base 110 of device 100 is shown. Mobile phone 200 is positioned in carriage 120 of device 100. Basket 41 as viewed is positioned in tray 131 in an xz plane with a length dimension defined by an x-dimension and a width dimension defined by a z dimension. In this manner, basket 41 includes five columns and dozens of rows with the column and row array defining cells with each cell representing a position for a cassette (e.g., cassette 30A or cassette 30B). As described above, basket 41 may not have individual defined cells. Instead, basket 41 may include partitions, such as partitions 405 and 410 that divide the basket into sections but not cells, with partitions 405 defining columns as described in this paragraph. "Cells" as used herein can be the space occupied by a cassette in the basket in a stacked arrangement with other cassettes or, in the case where a cassette is missing in a column, that would be occupied by the cassette if it were present. While basket 41 is shown in device 100, it is appreciated that alternatively cassettes may be contained in another container (e.g., container 50, FIG. 1) or magazine (e.g., magazine 40, FIG. 1) or magazine(s) in a container in the device.

In one example, machine-readable, non-transitory instructions associated with controller 130 direct a movement of one of support or pedestal 115 and base 110 in a longitudinal direction with respect to the other so that mobile phone 200 can capture images of identifiers on tissue cassettes in multiple cells, such as capture images of identifiers on tissue cassettes in a row or rows (e.g., record identifiers associated with five cassettes in an array having five cells in a row). The instructions associated with controller 130 also direct the movement of one of support or pedestal 115 and base 110 in a longitudinal direction with respect to the other so that, once any identifiers in a row are captured (e.g., recorded), the camera array associated with mobile phone 200 can capture (e.g., record) any identifiers on cassettes in an adjacent row or rows. The instructions associated with controller 130 further direct the process of movement of one of support or pedestal 115 and base 110 in a longitudinal direction with respect to the other and image capture (e.g., record) continue until all identifiers in all rows are captured (e.g., recorded).

Figures 5A, 5B, 5C:
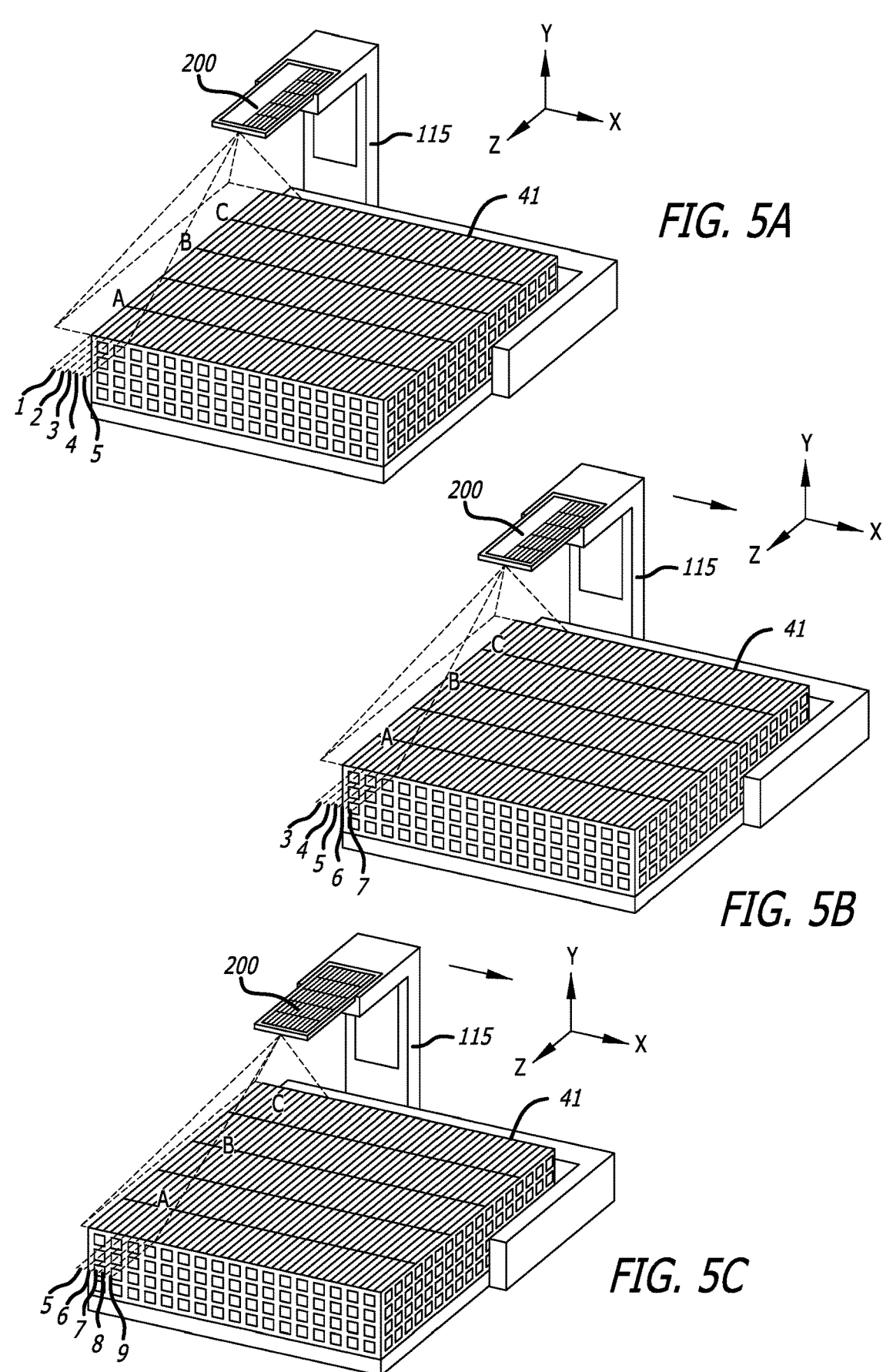
FIGS. 5A-5C show a representative step by step capture of images of cassettes in a basket or container.

FIGS. 5A-5C illustrate an example of the capture of images by mobile phone 200 in device 100. In this example, basket 41 is placed in device 100 (e.g., in drip tray 131 alone or basket 41 is placed in container 50 and container 50 and basket 41 are both placed in drip tray 131). Basket 41 may be as described above with respect to FIG. 1 and comprise five columns (z-direction) and dozens of rows (x-direction) with the column and row array defining cells with each cell representing a position of/for a cassette (e.g., cassette 30A, cassette 30B/frame 31B). To begin an image capturing process, mobile phone 200 may be placed in carriage 120 and a user may initiate an execution of the non-transitory, machine-readable program instructions in mobile phone 200 by, for example, running an application or program. In one example, the instructions in mobile phone 200 include instructions to controller 130 to position carriage 120 and mobile phone 200 in an initial or start position for imaging. The instructions may be contained in an application or other software program contained in mobile phone 200. When a user is ready to sense, capture and/or interpret an identifier on one or more cassettes in basket 41, the user starts the application or software program on mobile phone 200. Once started, mobile phone 200 communicates with controller 130 of device 100. Upon receipt of the instructions from mobile phone 200, non-transitory instructions associated with controller 130 are executed that direct a movement of pedestal 115 to an initial or start position. A start position may be a position of pedestal, for example, at an end of base 110 (e.g., a left end or side as viewed). Once carriage 120 and mobile phone 200 are in the initial or start position, the instructions associated with controller 130 alert mobile phone 200 that carriage 120 and mobile phone 200 are in the initial or start position. Instructions in mobile phone 200 may then cause mobile phone 200 to begin a capture of images of cassettes in basket 41. As illustrated in FIG. 5A, a focal width of a lens of mobile phone 200 may be capable of capturing cassettes in multiple rows (e.g., 10 rows) and in each column (e.g., 5 columns) in a single image. A focal width of mobile phone 200 cannot, in this example, encompass or include an entire area containing cassettes defined by an interior of basket 41. In this example, an x-direction of basket 41 is greater than a focal width in an x-direction of mobile phone 200. An initial or start position may position a lens or lenses of mobile phone 200 to capture an area preceding or before a leading edge of basket 41 (a xz area to the left of basket 41 as viewed). For example, an initial or start position may position a lens or lenses of mobile phone 200 to capture an area representatively equivalent to five rows in basket 41. In the example where a focal width of a lens of mobile phone 200 may be capable of capturing cassettes in 10 rows in each column (e.g., 5 columns) in a single image, a first image captured by a lens or lenses of mobile phone 200 will capture an area outside of basket 41 of a size of approximately five rows as well as the first five rows in basket 41. As one example, instructions associated with controller 130 direct a longitudinal (x-direction) movement of pedestal 115 with respect to base 110 (e.g., left to right movement, right to left movement). As pedestal 115 moves, mobile phone 200 in pedestal 115 moves left to right at a rate that allows capture of a distinct image of the captured rows (i.e., an image that is not substantially blurred). A representative rate of a longitudinal (x-direction) movement of pedestal 115 with respect to base 110 (e.g., left to right movement) may be on the order of 0.2 inches/seconds to 0.8 inches/second, such as 0.3 inches/second to 0.6 inches/second. To complete a capture or scan of a 200 mm basket at a rate of 0.3 inches/second is about 30 seconds. A maximum rate of longitudinal movement may be dictated by camera components associated with mobile phone 200 (e.g., the speed at which individual images may be sequentially captured). Instructions associated with mobile phone 200 that direct mobile phone 200 to capture images at a rate of, for example, two, three, four or more per second may allow for multiple images of cassettes in each row to be captured. For example, where a focal width of a lens of mobile phone 200 may be capable of capturing cassettes in 10 rows in each column and the start position includes the focal width including the first five rows and an area approximately five rows in size outside basket 41 (to the left of basket 41 as viewed) images of cassettes in the first row will be captured multiple times as the focal width in subsequent positions includes more and more rows as mobile phone 200 is moved longitudinally (e.g., rows 1-6, rows 1-7, rows 1-8, rows 1-9, and rows 1-10). The multiple images of each row also provides images of the cassettes at different angles as the lens of mobile phone 200 is moved.

FIGS. 5A-5C demonstrate a method wherein images of segments or portions of area of basket 41 (cassettes in basket 41) are captured by mobile phone 200. FIG. 5A shows a single image captured by mobile phone 200 (see the screen of mobile phone 200 representative of a captured image) that includes an xz area to the left of basket 41 and of rows 1-5 in basket 41 and each column (5 rows×5 columns=25 cassette images). Where basket 41 in drip tray 131 is not positioned so that mobile phone 200 can capture an image of, for example, cassettes in each row of the basket (e.g., a focal width of mobile phone 200 cannot extend across a z-direction width of basket 41 because of a position of carriage 120/phone 200 relative to the basket), prior to capturing images of the cassettes in basket 41, instructions associated with controller 130 include instructions to move drip tray 131 and basket 41 in a z-direction inward or outward so that images of each row of basket 41 can be captured.

Instructions associated with mobile phone 200 direct mobile phone 200 to capture images at a representative rate of two images per second, such as three images per second, such as four images per second, such as five images per second, or such as six images per second. Instructions associated with controller 130 direct a longitudinal (x-direction) movement of pedestal 115 with respect to base 110

(e.g., left to right movement) at a rate on the order of 0.2 inches/seconds to 0.8 inches/second, such as 0.3 inches/second to 0.6 inches/second. FIG. 5B representatively shows device 100 including mobile phone 200 capturing a second image of cassettes in basket 41 (e.g., three seconds after the image captured in FIG. 5A). In FIG. 5B, pedestal 115 has moved to the right causing the image captured by mobile phone 200 to be of rows 3-7 in basket 41 and each column. FIG. 5C shows a third image captured by mobile phone 200 that includes cassettes in rows 5-9 and each column. The longitudinal movement of pedestal 115 with respect to base 110 and the consecutive image capture by mobile phone 200 continues as described until an area of basket 41 has been covered (until mobile phone 200 captures images of all rows in basket 41).

In one example, as mobile phone 200 captures images of cassettes in basket 41, mobile phone 200 includes non-transitory instructions to read an identifier on each cassette and associate that cassette with a certain position in basket 41. The reading of captured identifiers may occur sequentially in the sense that the captured image of cassette identifiers in FIG. 5A is read before the captured image of cassette identifiers in FIG. 5B and the captured image of cassette identifiers in FIG. 5B is read before the captured image of cassette identifiers in FIG. 5C. In addition to reading of captured cassette identifiers, the instructions associated with mobile phone 200 may also identify a location of the cassettes in basket 41 such as according to a coordinate system for the cassettes in the basket (e.g., an xz position of each cassette in basket 41). The first captured image by mobile phone 200 illustrated in FIG. 5A may be considered a fixed image. The first image may have a representative size of 4032 pixels (x-direction) by 3024 pixels (z-direction) (12 megapixels). Using the example of FIG. 5A, where the captured image includes cassettes in rows 1-5 and an area preceding or before a leading edge of basket 41, the area preceding or before a leading edge of basket 41 may have a known or predetermined size, for example, occupying half of the x-direction pixels or an area of 2016 pixels (x-direction) by 3024 pixels (z-direction). Instructions associated with mobile phone 200 may include instructions to subtract the area preceding or before a leading edge of basket 41 which translates to an area of rows 1-5 occupying 2016 pixels by 3024 pixels (4032 pixels–2016 pixels=2016 pixels). Instructions in mobile phone 200 may provide that a location of the cassettes in rows 1-5 can be identified by their xz-pixel coordinates and a location of each is established.

As described in FIGS. 5A-5C, the continuous consecutive capture of images by mobile phone 200 may lead to a capture of multiple images of the same cassette. For example, in the first image captured by mobile phone 200 in FIG. 5A, a field of view of mobile phone 200 (a sensor or sensors of mobile phone 200) allows a capture of images of cassettes in rows 1-5. As pedestal 115 is moved, a field of view of mobile phone 200 changes to allow a capture of cassettes in rows 1-7 (FIG. 5B). Images of rows 1-5 were thus captured twice (in the first image and in the second image). Instructions associated with mobile phone 200 include instructions to determine if an identifier on a cassette at a particular location has previously been captured and read and, if so, to ignore or discard any subsequent duplicate reading of that identifier. One way this may be done is through instructions that compare identifiers at the same location read in different captured images (e.g., starting from a first captured image of an identifier of a particular cassette and determine if the captured image of the identifier has or can be read; if the identifier in that first captured image can be read, if that same identifier on that same cassette is captured in a subsequent captured image (e.g., a second captured image), identify that subsequent captured image as a duplicate and discard or ignore the duplicate (e.g., do not save the subsequent captured image of the identifier).

The capturing of duplicate images may be utilized to effectively capture and read identifiers on each cassette in basket 41. It may be appreciated, that depending on an angle of a lens or lenses of mobile phone 200 and a position of a cassette in basket 41, one image may not capture a readable image of an identifier on the cassette. As pedestal 115 moves, an angle of a lens or lenses of mobile phone 200 and a position of a cassette in basket 41 changes. Such a change may allow a second image of the cassette to provide a better image of its identifier and allow the identifier to be read. In the example illustrated in FIGS. 5A-5C, images are captured of each cassette at least two times at two different phone angles. It is appreciated that the number of images captured of each cassette may vary depending on a velocity of pedestal 115 and a rate of image capture of mobile phone 200. In one example, images of each cassette in basket 41 are captured at least twice, such as at least three times, such as at least four times, such as at least five times, such as at least six times at a representative frame rate of 24 frames per second (fps), 30 fps or 60 fps, etc.

The capturing of individual identifiers on cassettes may be improved using dynamic focusing of a lens or lenses of mobile phone 200. In one example, non-transitory instructions associated with mobile phone 200 may direct a focus point or area to shift between two or more areas, such as three or more areas in a lateral direction (z-direction), over basket 41 as controller 130 directs a longitudinal (x-direction) movement of mobile phone 200 to capture images of cassettes in basket 41 (e.g., controller directs a movement of pedestal 115 with respect to base 110 (e.g., left to right movement)). FIGS. 5A-5C representatively shows three different focus points or areas, identified as "A", "B" and "C", that mobile phone 200 might sequentially use as it captures images of identifiers in basket 41. The focus points "A", "B" and "C" represent different areas across a lateral (z-direction) distance or width of basket 41. For example, for a first image (which might be an image capture of 5 to 10 rows of cassettes), mobile phone 200 may have a focus of "A" which is an area of basket 41 furthest from pedestal 115 (e.g., an area focused on the furthest two columns of cassettes from pedestal 115). For a subsequent second image (e.g., immediately succeeding the first image), mobile phone 200 may have a focus of "B" that is an area in the center of basket 41 (e.g., an area focused on the furthest middle column of cassettes in basket 41) and for a still subsequent third image (e.g., immediately succeeding the second image), mobile phone may have a focus of "C" which is an area of basket 41 closest to pedestal 115 (e.g., an area focused on the nearest two columns of cassettes to pedestal 115). A focal distance between a lens or lenses of mobile phone 200 and a front side of cassettes in basket 41 may be different for each focus area. For example, a focal distance between a lens or lenses of mobile phone 200 and a front side of cassettes in basket 41 may be, for example, 5.5 inches (about 14 cm) in focus area B in the center of device 100 and basket 41 and a focal distance in focus area A and focus area C may be different than a focal length in focus area B (e.g., greater than 5.5 inches (14 cm)). The focus areas (e.g., "A", "B" and "C") and the switching between the areas (e.g., after each image capture, after two or more image captures, etc.) may be experimentally determined by repeated operations of image capture across an area of basket 41 and the information stored in a memory of mobile phone 200.

In one example, instructions associated with mobile phone 200 may direct a gathering of the captured images and, once duplicates of the identifier on the same cassette are identified and removed, the stitching together of the captured images and the making available an image of the entirety of basket 41 with all cassettes visible. The stitching together of captured images may also define a coordinate system for the cassettes in the basket (e.g., a xz position of each cassette in basket 41). Such stitching may be done after pedestal 115 has traversed an area of basket 41 (i.e., after images (e.g., multiple images) of all cassettes in basket 41 are obtained) or while pedestal 115 is traversing the area. One way stitching may be performed is by using pixel locations. As described above, as pedestal 115 traverses the area of basket 41, mobile phone 200 captures images that overlap due to the field of view of the sensor or sensors of the mobile phone and the velocity of traverse of pedestal 115. A first image captured by mobile phone 200 is, for example at one end of basket 41 (a start or initial position). A first image captured by mobile phone 200 may be considered a fixed image to which subsequent images are stitched to form an overall image. The first image may have a representative size of 4032 pixels by 3024 pixels (12 megapixels). After the first image is captured, pedestal 115/mobile phone 200 move in an x-direction a known distance (e.g., a known distance based on encoder information from motor 1109 related to distance traveled of pedestal 115/mobile phone 200) before the second image is captured. This known distance may be translated into pixels. If the distance equates, for example, to 1000 pixels in an x-direction, the second image overlaps the first image by an identifiable 9.17 megapixels (4032 pixels −1000 pixels=3032 pixels; 3032 pixels×3024 pixels=9.17 megapixels). Successive images would overlap similarly. The identifiable 9.17 megapixels from each of the second through final image may be used for the purpose of identifying identifiers on cassettes in basket 41, but instructions associated with phone 200 when executed will identify such pixels as overlapping pixels for stitching purposes and form a stitched image without duplicating the overlapped pixels. The pixels of each image captured by phone 200 provide a stitched image of known coordinates (i.e., a coordinate system of x-coordinates and z-coordinates).

Once pedestal 115 has traversed an area of basket 41 and captured images of all cassettes in the basket (e.g., multiple images of each cassette), executed instructions associated with mobile phone 200 determine if an identifier associated with each cassette in basket 41 has been read. In certain instances, it may be difficult for a readable image of an identifier on a cassette in basket 41 to be obtained by traversing a basket area through the longitudinal movement of pedestal 115. If it is determined that an identifier on any cassette in basket 41 cannot or has not been read (e.g., images taken of a cassette through the longitudinal (x-direction) movement of pedestal 115 did not provide a readable image of an identifier of a cassette), using the coordinate system determined by executed instructions from mobile phone 200 as well as possible encoder information from motor 1109 related to distance traveled of pedestal 115/mobile phone 200, instructions associated with phone 200 may direct controller 130 to direct a longitudinal (x-direction) movement of pedestal 115 and/or a lateral (z-direction) movement of drip tray 131/basket 41 so that a lens or lenses of phone 200 is or are at a desired position to capture an image of the unread identifier and to capture one or more images of the identifier. A desired position may be, for example, positioning a lens or lenses of phone 200 directly over the unread identifier. A desired position may also be more than one position of the lens or lenses of phone 200 relative to the unread identifier. For example, a lens or lenses of phone 200 may be positioned around an unread identifier (e.g., step around an area above the cassette). Instructions associated with mobile phone 200 direct phone 200 to capture images and transmit the images of the cassette identified as having an unread identifier until mobile phone 200 can read the identifier. Once mobile phone 200 can read the identifier of the cassette identified as having an unread identifier, the instructions associated with controller 130 direct a movement of pedestal 115 and/or drip tray 130/ basket 41 to a position over any other cassette identified as a having an identifier that is unread and repeat the process of capturing additional images. In an instance where even after capturing one or more additional images, if an unread identifier still cannot be read, instructions associated with mobile phone 200 may alert an operator to inspect the cassette or enter it manually. Mobile phone 200 may use digital imaging processing to produce an image of an identifier that may be read by the phone. Such digital imaging processing may use color filters to reproduce color in a digital image. In certain instances, it may be less challenging for mobile phone 200 to read an identifier on a cassette (e.g., to read an unread identifier) if a color filter is removed. In one example, for a mobile phone using colored filters (e.g., red, green, blue filters), instructions associated with mobile phone 200 may direct that one or more of such filters be suppressed during digital imaging processing and reading of an identifier.

In some instances, each cell of an array in basket 41 may or may not contain a tissue cassette. In order to identify whether a tissue cassette is present in a cell, device 100 may include a sensor system. Referring again to FIG. 3, device 100 includes sensor bar 170 connected to support or pedestal 115 directly or indirectly by connection to carriage 120 and projecting in a z-direction above basket 41. Sensor bar 170 includes a number of sensors 1705 each positioned to be facing downward toward basket 41. Sensors 1705 are positioned in a linear arrangement on sensor bar 170 to align with columns in basket 41. Sensors 1705 are, for example, photoelectric sensors each including an emitter for emitting light downward as viewed toward an individual cell in a column and a receiver for receiving reflected light. Sensors 1705 may be activated by machine-readable instructions contained in controller 130. When activated, each sensor directs (emits) light in a direction of a cell in a basket and receives at its receiver a reflection of that light. For example, if a cassette is present in a cell to which light is directed, sensor 1705 receives a reflection of the transmitted light. If no cassette was present in a cell, little or no reflection will be received by sensor 1705 because of the added distance of travel. The distance traveled and the absence/presence of the reflective sensor output together can be used by controller 130 via, for example, encoder information from motor 1109 to map a position of a cassette inside basket 41 (or inside a magazine or container as the case may be). When an identifier is not captured or read at a particular location in basket 41, the coordinates of that location can be determined and used to confirm the result. For example, instructions associated with mobile phone 200 can move mobile phone 200 (via pedestal 115) to directly over or near the particular location, once determined, and verify via, for example, an image capture of the particular location that a cassette is not present or, if a cassette is present, to capture another image of an identifier associated with that cassette.

Device 100 may include external illumination. FIG. 3 shows sensor bar 170 including one or more light sources 1710 such as light emitting diodes (LEDs) along its length. Light sources 1710 are directed at basket 41 in drip tray 131. Light sources 1710 may aid in illuminating cassettes (identifiers on cassettes) in basket 41. Instructions associated with controller 130 may include instructions to power the one or more light sources to emit light during image capture by phone 200. For example, mobile phone 200 will know when a user presses a button to Start a scan of cassettes. At that time, mobile phone 200 will send a command to controller 130 to move the various motors to position basket 41 and mobile phone 200 in a start position for a scan (e.g., motor 1206 may move pedestal in a y-direction (see FIG. 2); motor 1116 may move drip tray in a z-direction (see FIG. 2); and or motor 1109 may move pedestal in an x-direction (see FIG. 4)). Instructions from mobile phone 200 or from controller 130 may then turn light sources 1710 on before a scan of basket 41. With light sources 1710 turned on, instructions associated with mobile phone 200 include instructions to adjust the exposure automatically to get the best picture results (auto exposure). Instructions may also include instructions operable to adjust an intensity of light from light sources 1710 (e.g., in a dark ambient, an intensity might be greater than in a bright ambient). Light sources 1710 may be used to offer even or consistent illuminations across the entire picture taking areas and adjust the intensity for ambient light conditions. Without wishing to be bound by theory, it is believed that the use of light sources 1710 enhance an auto exposure function of a mobile phone, since the scene is already evenly or consistently illuminated.

Although FIG. 3 shows light sources 1710 connected to sensor bar 170, it is appreciated that the one or more light sources may be connected to support or pedestal 115 or carriage 120 through an independent connection such as a light bar or bracket light bar placed, for example, so as to not interfere with the field of view of a lens or lenses of the mobile phone. A light source such as emanating from sensor bar 170 or a light bar or bracket is a source separate from a light source component of mobile phone 200 such as a flashlight feature or a camera flash. A light source separate from a light source component of mobile phone 200 reduces shadowing or blocking of identifiers by other cassettes in a basket, container or magazine that is being scanned. In one example, instructions associated with mobile phone 200 may include instructions to illuminate the flashlight on the mobile phone and/or use the camera flash during image capture of cassettes.

Device 100 may have different modes of operation. A first mode of operation is that mobile phone 200 associated with device 100 captures images of and reads identifiers associated with cassettes in a basket, magazine or container, determines a content of the basket, magazine or container (e.g., a basket with one or more empty locations), gathers coordinates of the cassettes and creates a panorama or overview image of the cassettes including colors and transfers the captured images, overview image and barcode information (content, color of cassettes, coordinates) as well as a date and time of read), to controller 130 through a wireless communication link. Controller 130 saves the identifiers into a database within controller 130. In a second mode of operation, mobile phone 200 may capture and read identifiers, determine a content of a basket, magazine or container (e.g., a basket with one or more empty locations), gather coordinates of the cassettes and create a panorama or overview image and store this information into an on-board database and also send it to an exterior system such as laboratory information systems (LIS)/laboratory information management systems (LIMS)/Middleware computer software. Mobile phone 200 may, for example, wirelessly or wired transmit the captured information to a LIS or other computer system. A third mode of operation is similar to the second mode but mobile phone 200 can also request the LIS/LIMS/Middleware computer software for tissue processing protocol information or can read the tissue processing protocol out of an identifier and analyze if there is any inconsistency related to tissue processing protocols between the cassettes. A fourth mode of operation allows mobile phone 200 to capture and read identifiers, determine a content of a basket, magazine or container (e.g., a basket with one or more empty locations), gather coordinates of the cassettes and create a panorama or overview image and save it into a database associated with mobile phone 200 and also to identify a color of a cassette and analyze if there is any inconsistency related to tissue processing protocols defined by a color of a cassette.

Figures 6, 7:
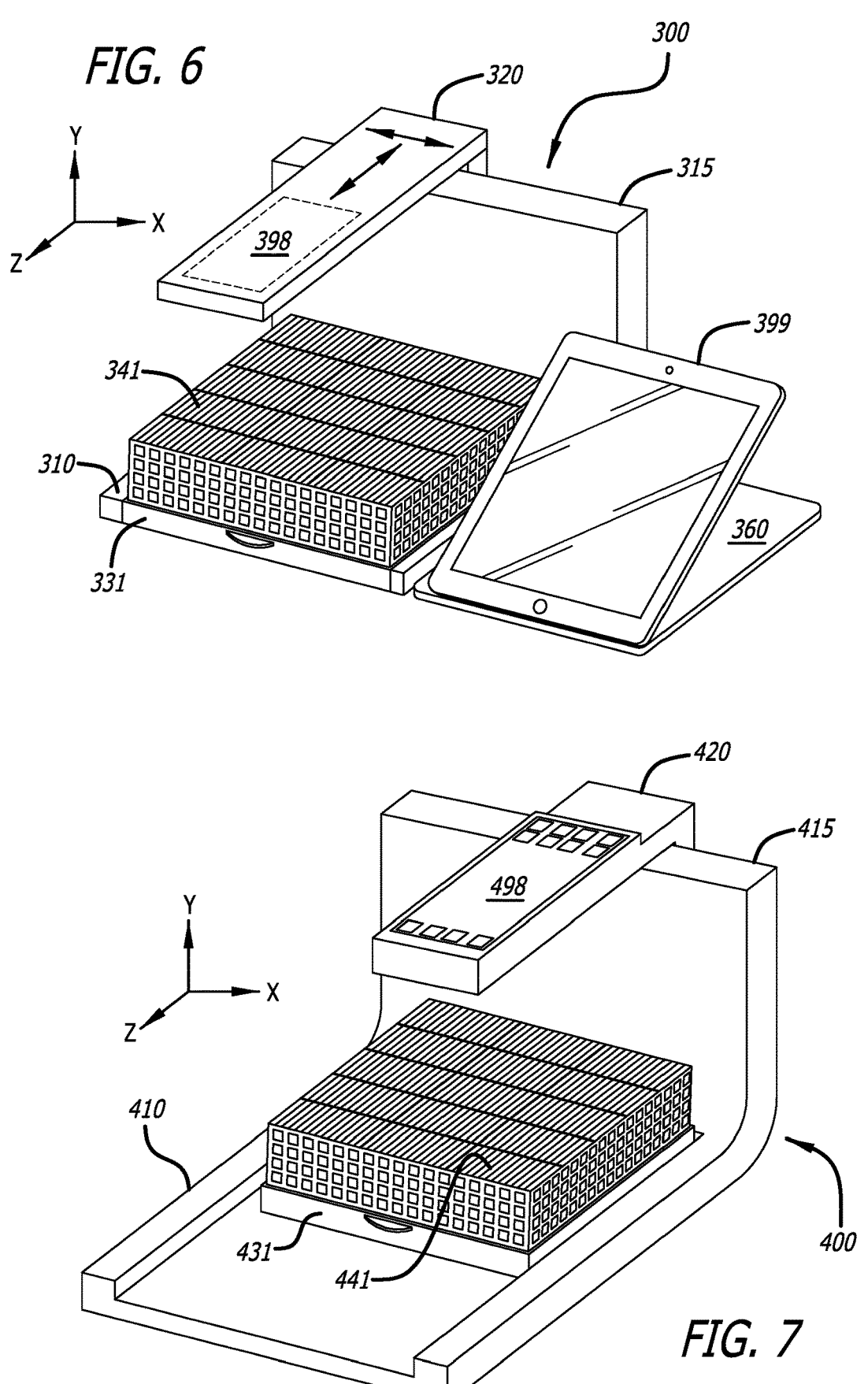
FIG. 6 shows a top, side perspective view of another example of a device that may be used to capture, store and output identification information such as a barcode on a sample carrier (e.g., a cassette or cassette/frame assembly) in an array such as in a basket or other container without removing the sample carrier from the basket or other container.
FIG. 7 shows a top, side perspective view of another example of a device that may be used to capture, store and output identification information such as a barcode on a sample carrier (e.g., a cassette or cassette/frame assembly) in an array such as in a basket or other container without removing the sample carrier from the array (e.g., magazine, basket or other container).

FIG. 6 shows another example of a device that may be used to capture, store and output identification information such as a barcode on a sample carrier (e.g., a cassette or cassette/frame assembly) in an array such as in a basket or other container without removing the sample carrier from the basket or other container. In this example, device 300 is operable to be mounted on a table or other surface and have sample carriers such as cassettes be brought to the device. Device 300 includes base 310 and carriage 320 connected to base 310 through support or pedestal 315. Carriage 320 projects a vertical or y-dimension distance from base 310 defined by a length of support or pedestal 315. Carriage 320 may be operable to contain a mobile phone, such as mobile phone 200. Disposed in base 310 is tray 331 that is operable to contain basket 341 (similar to basket 41 described above), one or more magazines or other container.

In this example, carriage 320 includes a shroud to cover a top side (screen side) of mobile phone 398. An underside of carriage 320 includes an opening to expose a lens of mobile phone 398. In this example, basket 341 (tray 331) is fixed. The positioning of a lens or lenses of mobile phone for the image capture of identifiers on cassettes in basket 341 is 398 is achieved by movement of carriage 320 in a longitudinal (x-) direction and a movement of mobile phone 398 in a lateral (z-) direction as necessary. The longitudinal movement of carriage 320 may representatively be performed by a motor driven lead screw positioned inside a body of base 310 (similar to lead screw 1106/bracket 1108/motor 1109 described above with reference to FIG. 4. A lead or ball screw and motor set-up can be disposed in carriage 320 and be operable to move mobile phone 398 in a longitudinal direction. Device 300 may include a controller such as positioned in pedestal 315 or other location to control the movement of carriage 320 and mobile phone 398 and communicate with mobile phone 398 similar to controller 130 in device 100 and the description with respect to FIGS. 2-5C as an example).

In the example of FIG. 6, device 300 may include area 360 longitudinally adjacent base 310 or part of base 310 for a display device to display data obtained by mobile phone 398. As one example, display device 399 may be a tablet (e.g., an iPad) or other computer monitor or computer device (e.g., laptop, desktop). Display device may be operable to display images captured by mobile phone 398 as well as movement the mobile phone (e.g., display images as mobile phone 398 moves left to right or right to left). Device 300 may have a connection to hardwire display device 399 to device 300 or the connection between display device 399 and device 300 and mobile phone 398 may be wireless. It is appreciated that, although area 360 may be provided, in another example, display device 399 may be set up on the same desk or table top as device 300 or a separate location (e.g., a separate desk or table).

FIG. 7 shows another example of a device that may be used to capture, store and output identification information such as a barcode on a sample carrier (e.g., a cassette or cassette/frame assembly) in an array such as in a basket or other container without removing the sample carrier from the basket or other container. In this example, device 400 is operable to be mounted on a table or other surface and have sample carriers such as cassettes be brought to the device. Device 400 includes base 410 and carriage 420 connected to base 410 through support or pedestal 415. Carriage 420 projects a vertical or y-dimension distance from base 410 defined by a length of support or pedestal 415. Carriage 420 may be operable to contain a mobile phone, such as mobile phone 498. Disposed in base 410 is tray 431 that is operable to contain basket 441 (similar to basket 41 described above with respect to device 100), one or more magazines or other container.

Figure 8:
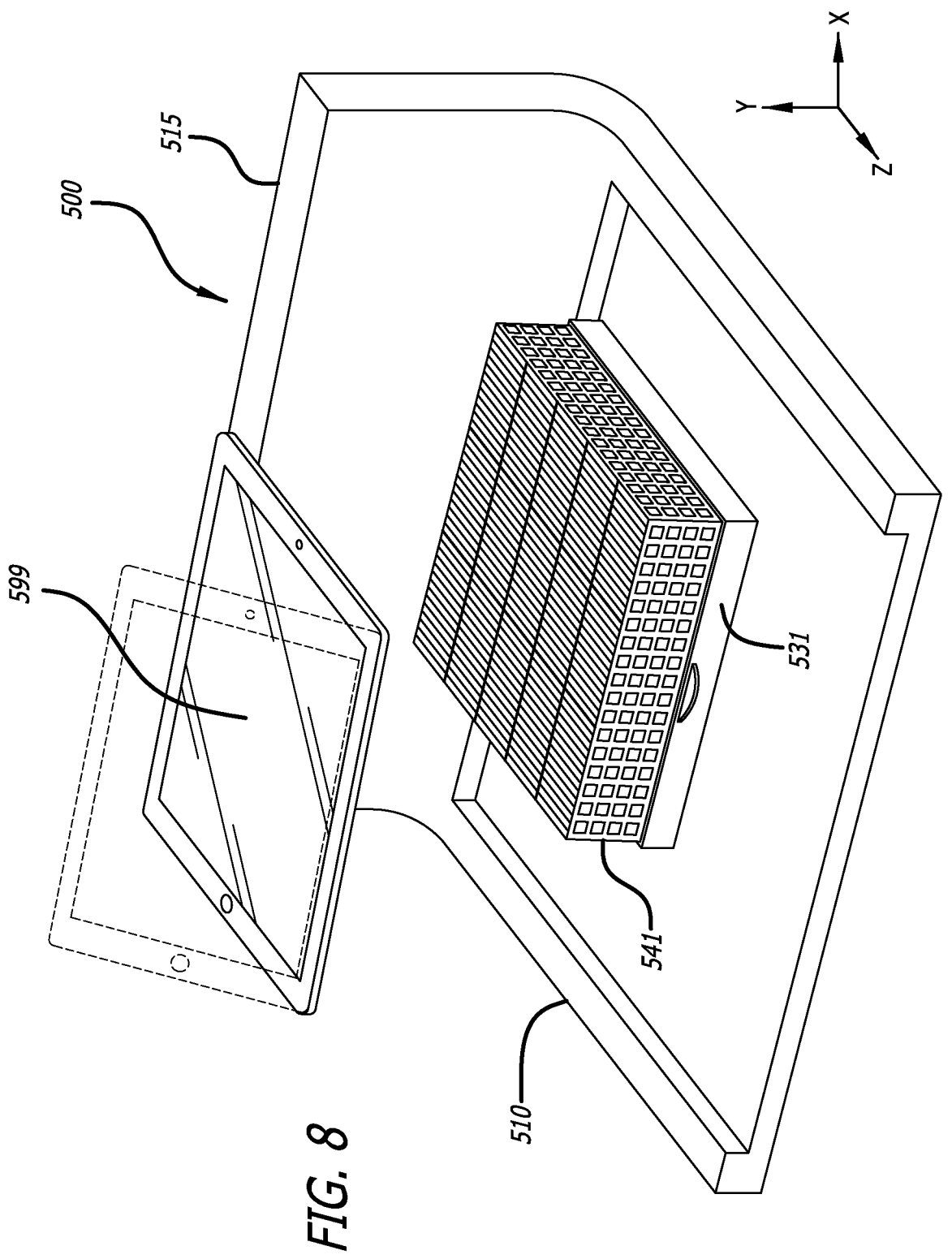
FIG. 8 shows a top, side perspective view of another example of a device that may be used to capture, store and output identification information such as a barcode on a sample carrier (e.g., a cassette or cassette/frame assembly) in an array such as in a basket or other container without removing the sample carrier from the array (e.g., magazine, basket or other container).

In the example of FIG. 7, mobile phone 498 is disposed in carriage 420 with a lens or lenses of mobile phone 498 exposed on an underside of carriage 420 to allow the capture of identifiers on cassettes in basket 441. Carriage 420 is operable to move in a longitudinal (x-) direction with respect to base 410. Tray 431 in base 410 is operable to move in a lateral (z-) direction. The positioning of mobile phone 498 for capturing images of and reading identifiers on cassettes in basket may be controlled by a controller in device 400 and the movement of each of carriage 420 and tray 431 may be performed, for example, using a lead screw/bracket/motor configuration in a similar manner as that described with respect to device 100. FIG. 8 shows another example of a device that may be used to capture, store and output identification information such as a barcode on a sample carrier (e.g., a cassette or cassette/frame assembly) in an array such as in a basket or other container without removing the sample carrier from the basket or other container. In this example, device 500 is operable to be mounted on a table or other surface and have sample carriers such as cassettes be brought to the device. Device 500 includes base 510 and carriage 520 connected to base 510 through support or pedestal 515. Carriage 520 projects a vertical or y-dimension distance from base 510 defined by a length of support or pedestal 515. Carriage 520 may be operable to contain a mobile phone, such as mobile phone 599 which, in this example, is a tablet such as an iPad. Carriage 520 may include a hinge mechanism allowing mobile phone 599 to be held or supported at different angles in carriage 520. For example, mobile phone 599 can be positioned horizontally or one end of the mobile phone may be raised (e.g., a top end or an end closest to support or pedestal 515) at an angle relative to its opposite end to improve user viewing and/or image capture. Disposed in base 510 is tray 531 that is operable to contain basket 541 (similar to basket 41 described above with respect to device 100), one or more magazines or other container.

In the example of FIG. 8, mobile phone 599 is disposed in carriage 520 with a lens or lenses of mobile phone 599 exposed on an underside of carriage 520 to allow the capture of identifiers on cassettes in basket 541. In this example, carriage 520 is stationary (i.e., carriage 520 is not operable to move in a longitudinal (x-) direction or lateral (z-)

direction with respect to base 510. Tray 531 in base 510 is operable to move in both a longitudinal (x-) direction and a lateral (z-) direction. The positioning of mobile phone 599 for capturing images of and reading identifiers on cassettes in basket may be controlled by a controller in device 500 and the movement of tray 531 may be performed, for example, using a lead screw/bracket/motor configuration in a similar manner as that described with respect to device 100.

The imaging device and systems described allows capturing and reading of identifiers (e.g. barcodes) of individual cassettes assembled together with other cassettes without removing a cassette from other cassettes in a magazine or basket or other container. Whereas specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims and aspects appended and any and all equivalents thereof.

Aspects

The following are aspects of the invention.

1. An apparatus to identify an identifier on a tissue cassette in an assembly of a plurality of tissue cassettes comprising:
 a base operable to be mounted on a tabletop;
 a carriage coupled to the base and projecting a distance above the base, the carriage operable to contain a mobile phone comprising a camera array in a position such that the camera array faces in a direction of the base; and
 a controller coupled to the carriage, the controller comprising machine-readable instructions operable to direct a movement of one of the carriage and the base in a direction with respect to the other along an axis.

2. The apparatus of Aspect 1, wherein the base comprises an orientation designation for a container operable to contain an assembly of a plurality of cassettes.

3. The apparatus of Aspect 2, wherein the direction movement of the one of the carriage and the base is operable to allow the capture of images by a camera of a mobile phone of identifiers on a plurality of tissue cassettes in a container positioned below the mobile phone in the carriage.

4. The apparatus of any of Aspects 1-3, further comprising a sensor bar coupled to the carriage, the sensor bar comprising one or more photoelectric sensors, the one or more photoelectric sensors comprising an emitter for emitting light in a field of view of a camera array of a mobile phone contained in the carriage and a receiver for receiving reflected emitted light.

5. The apparatus of Aspect 4, wherein the sensor bar comprises a plurality of photoelectric sensors arranged linearly on the sensor bar and spaced to correspond to a spacing of tissue cassettes arranged in rows in a basket positioned below a mobile phone in the carriage.

6. The apparatus of claim 4, wherein the carriage is operable to move in the direction with respect to the base and the sensor bar is operable to be moved with the carriage.

7. The apparatus of any of Aspects 1-6, further comprising at least one light source coupled to the carriage operable to emit light from the at least one light source at the base.

8. The apparatus of any of Aspects 1-7, further comprising a tray operable to be removably positioned in the base, the tray comprising dimensions to accommodate a container operable to contain an assembly of a plurality of cassettes.

9. The apparatus of Aspect 8, wherein in the tray is operable to move in a direction along an axis orthogonal to the axis of the movement of one of the carriage and the base.

10. The apparatus of any of Aspects 1-9, further comprising a charger coupled to the carriage and operable to charge a mobile phone contained in the carriage.

11. The apparatus of Aspect 10, wherein the charger is operable to provide a wireless charging connection for a mobile phone.

12. The apparatus of any of Aspects 1-11, wherein the machine-readable instructions comprise instructions to move the one of the carriage and the base in a direction with respect to the other along the axis based on instructions received from a mobile phone contained in the carriage.

13. An assembly comprising:
 the apparatus of any of Aspects 1-12; and
 a mobile phone in the carriage of the device, the mobile phone comprising non-transitory machine-readable instructions operable to direct the apparatus to move the one of the carriage and the base in a direction with respect to the other along the axis and operable to capture images during the movement.

14. A method comprising:
 placing a mobile phone in a carriage that is coupled to and projects a distance above a base;
 placing a container below the carriage, the container comprising a plurality of tissue cassettes, wherein each of the plurality of tissue cassettes comprises an identifier on a front face thereof; and
 capturing by the mobile phone of an image of the identifier on each of the plurality of tissue cassettes while the plurality of tissue cassettes remain in the container.

15. The method of Aspect 14, further comprising:
 reading by the mobile phone of the captured identifier on each of the plurality of tissue cassettes.

16. The method of Aspect 14 or Aspect 15, wherein capturing by the mobile phone of an image of the identifier on each of the plurality of tissue cassettes comprises successively capturing more than one image of the identifier while one of the carriage and the base move in a direction with respect to the other along an axis.

17. The method of Aspect 16, wherein successively capturing more than one image comprises capturing a first image of a first area of the container before capturing a second image of a second area of the container and a portion of the second area overlaps a portion of the first area.

18. The method of Aspect 17, further comprising:
 reading the captured identifier on each of the plurality of tissue cassettes in each of the first image and the second image; and
 comparing the read captured identifier on each of the plurality of tissue cassettes in the first image with the read captured identifier on each of the plurality of tissue cassettes in the second image; and
 identifying any duplicates of the read captured identifier on each of the plurality of tissue cassettes in the first image with the read captured identifier on each of the plurality of tissue cassettes in the second image.

19. The method of any of Aspects 14-18, further comprising stitching by the mobile phone of an overall image of the one or more cassettes in the container from the successively captured images.

20. The method of any of Aspects 14-19, wherein successively capturing more than one image comprises capturing a first image of an identifier with a first focus position on the container and a second image of the identifier with a second focus position on the container, wherein a direction of a change from the first focus position to the second focus position is different than the direction of movement of the one of the carriage and the base.

21. A machine-readable medium comprising non-transitory instructions that when executed by a mobile phone comprise a method comprising:

directing an apparatus comprising a carriage coupled to and projecting a distance above a base to move one of the carriage and the base in a direction with respect to the other along an axis;

in response to the movement, capturing successive images by the mobile phone in the carriage of an area below the carriage; and stitching the successive images into an overall image.

22. The machine-readable medium of Aspect 20, wherein capturing images comprises capturing successive images comprises capturing a first image of a first area before capturing a second image of a second area and a portion of the second area overlaps a portion of the first area.

23. The machine-readable medium of Aspect 20 or Aspect 21, wherein the area below the carriage comprises a plurality of cassettes each comprising an identifier and the executed non-transitory instructions comprise a method further comprising:

reading of an identifier of each of the plurality of cassettes.

24. The machine-readable medium of Aspect 22, wherein the mobile phone comprises digital processing comprising one or more color filters to reproduce a captured image and prior to reading of the identifier of at least one of the plurality of cassettes, method comprises removing the one or more color filters.

25. The machine-readable medium of Aspect 20, wherein the executed non-transitory instructions comprise a method further comprising:

transmitting the stitched image to an exterior system.

Whereas specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims and aspects appended and any and all equivalents thereof.

What is claimed is:

1. An apparatus to identify an identifier on a tissue cassette in an assembly of a plurality of tissue cassettes comprising:

a base operable to be mounted on a tabletop;

a carriage coupled to the base and projecting a distance above the base; and a controller coupled to the carriage, the controller comprising machine-readable instructions operable to direct a movement of one of the carriage and the base in a direction with respect to the other along an axis; and a mobile phone contained in the carriage, the mobile phone comprising (1) a camera array in a position such that the camera array faces in a direction of the base and (2) machine-readable instructions to:

direct an automatic capture of images of an identifier on each tissue cassette contained in a container of an assembly of a plurality of tissue cassettes arranged in the base at a rate providing for more than one image of an identifier on each tissue cassette in the plurality of tissue cassettes to be successively captured and wherein each capture of images encompasses a field of view that is less than an area of the container; and read the identifier on each tissue cassette in each captured image; and discard or ignore any identifier in a captured image that has been read from a previous image.

2. The apparatus of claim 1, wherein the base comprises an orientation designation for a container operable to contain an assembly of a plurality of cassettes.

3. The apparatus of claim 2, wherein the direction of movement of the one of the carriage and the base is operable to allow the capture of images by the camera of the mobile phone of identifiers on a plurality of tissue cassettes in a container positioned below the mobile phone in the carriage.

4. The apparatus of claim 1, further comprising a sensor bar coupled to the carriage, the sensor bar comprising one or more photoelectric sensors, the one or more photoelectric sensors comprising an emitter for emitting light in a field of view of a camera array of a mobile phone contained in the carriage and a receiver for receiving reflected emitted light.

5. The apparatus of claim 4, wherein the sensor bar comprises a plurality of photoelectric sensors arranged linearly on the sensor bar and spaced to correspond to a spacing of tissue cassettes arranged in rows in a basket positioned below a mobile phone in the carriage.

6. The apparatus of claim 4, wherein the carriage is operable to move in the direction with respect to the base and the sensor bar is operable to be moved with the carriage.

7. The apparatus of claim 1, further comprising at least one light source coupled to the carriage operable to emit light from the at least one light source at the base.

8. The apparatus of claim 1, further comprising a tray operable to be removably positioned in the base, the tray comprising dimensions to accommodate a container operable to contain an assembly of a plurality of cassettes.

9. The apparatus of claim 8, wherein in the tray is operable to move in a direction along an axis orthogonal to the axis of the movement of one of the carriage and the base.

10. The apparatus of claim 1, further comprising a charger coupled to the carriage and operable to charge a mobile phone contained in the carriage.

11. The apparatus of claim 10, wherein the charger is operable to provide a wireless charging connection for a mobile phone.

12. The apparatus of claim 1, wherein the machine-readable instructions associated with the controller comprise instructions to move the one of the carriage and the base in a direction with respect to the other along the axis based on instructions received from the mobile phone contained in the carriage.

13. The apparatus of claim 1, wherein the mobile phone comprises non-transitory machine-readable instructions operable to direct the one of the carriage and the base to move in a direction with respect to the other along the axis.

14. A method comprising:

placing a mobile phone in a carriage that is coupled to and projects a distance above a base;

placing a container below the carriage, the container comprising a plurality of tissue cassettes, wherein each of the plurality of tissue cassettes comprises an identifier on a front face thereof, with the front face of each of the plurality of tissue cassettes facing the carriage;

successively capturing by the mobile phone of more than one image of the identifier on each of the plurality of tissue cassettes while the plurality of tissue cassettes remain in the container while one of the carriage and the base move with respect to the other such that each of the more than one image of the identifier on each of the plurality of tissue cassettes is captured in a distinct field of view of the mobile phone that is less than an area of the container;

reading each of the successively captured more than one image of the identifier on each of the plurality of tissue cassettes; and discarding or ignoring any identifier that has been read by a previously captured image.

15. The method of claim 14, further comprising:

reading by the mobile phone of the captured identifier on each of the plurality of tissue cassettes.

16. The method of claim 14, wherein successively capturing more than one image comprises capturing a first image of a first area of the container before capturing a second image of a second area of the container and a portion of the second area overlaps a portion of the first area.

17. The method of claim 14, further comprising stitching by the mobile phone of an overall image of the one or more cassettes in the container from the successively captured images.

18. A machine-readable medium comprising non-transitory instructions that when executed by a mobile phone comprise a method comprising:

directing an apparatus comprising a carriage coupled to and projecting a distance above a base to move one of the carriage and the base in a direction with respect to the other along an axis;

in response to the movement, capturing successive images by the mobile phone in the carriage of an area below the carriage comprising a container, the container comprising a plurality of tissue cassettes, wherein each of the plurality of tissue cassettes comprises an identifier on a front face thereof, with the front face of each of the plurality of tissue cassettes facing the carriage, and wherein capturing successive images comprise more than one image of each of the plurality of tissue cassettes in the container captured while the one of the carriage and the base move with respect to the other such that each of the more than one image of the identifier on each of the plurality of cassettes is captured in a distinct field of view of the mobile phone that is less than an area of the container;

reading each of the successively captured more than one image of the identifier on each of the plurality of tissue cassettes;

discarding or ignoring any identifier that has been read by a previously captured image; and stitching the successive images into an overall image.

19. The machine-readable medium of claim 18, wherein capturing successive images comprises capturing a first image of a first area before capturing a second image of a second area and a portion of the second area overlaps a portion of the first area.

20. The machine-readable medium of claim 18, wherein the mobile phone comprises digital processing comprising one or more color filters to reproduce a captured image and prior to reading of the identifier of at least one of the plurality of cassettes, method comprises removing the one or more color filters.

21. The machine-readable medium of claim 18, wherein the executed non-transitory instructions comprise a method further comprising:

transmitting the stitched image to an exterior system.

22. The method of claim 14, wherein successively capturing more than one image comprises capturing a first image of an identifier with a first focus position on the container and a second image of the identifier with a second focus position on the container, wherein a direction of a change from the first focus position to the second focus position is different than the direction of movement of the one of the carriage and the base.

23. The machine-readable medium of claim 18, wherein capturing successive more than one image comprises capturing a first image of an identifier with a first focus position on the container and a second image of the identifier with a second focus position on the container, wherein a direction of a change from the first focus position to the second focus position is different than the direction of movement of the one of the carriage and the base.

* * * * *